(12) United States Patent
Hancock et al.

(10) Patent No.: US 12,396,784 B2
(45) Date of Patent: Aug. 26, 2025

(54) ELECTROSURGICAL RESECTOR TOOL

(71) Applicant: CREO MEDICAL LIMITED, Monmouth (GB)

(72) Inventors: Christopher Paul Hancock, Bath (GB); Louis Turner, Chepstow (GB); Patrick Burn, Chepstow (GB); Malcolm White, Chepstow (GB); Simon Meadowcroft, Chepstow (GB); George Christian Ullrich, Chepstow (GB); David Edward Webb, Chepstow (GB)

(73) Assignee: Creo Medical Limited, Chepstow (GB)

( * ) Notice: Subject to any disclaimer, the term of this patent is extended or adjusted under 35 U.S.C. 154(b) by 337 days.

(21) Appl. No.: 16/651,101

(22) PCT Filed: Oct. 12, 2018

(86) PCT No.: PCT/EP2018/077880
§ 371 (c)(1),
(2) Date: Mar. 26, 2020

(87) PCT Pub. No.: WO2019/073037
PCT Pub. Date: Apr. 18, 2019

(65) Prior Publication Data
US 2020/0222112 A1 Jul. 16, 2020

(30) Foreign Application Priority Data
Oct. 13, 2017 (GB) ...................................... 1716865

(51) Int. Cl.
*A61B 18/14* (2006.01)
*A61B 18/00* (2006.01)
*A61B 18/18* (2006.01)

(52) U.S. Cl.
CPC ...... *A61B 18/1447* (2013.01); *A61B 18/1492* (2013.01); *A61B 18/1815* (2013.01);
(Continued)

(58) Field of Classification Search
CPC ............ A61B 18/1815; A61B 18/1447; A61B 18/1492; A61B 18/1442; A61B 18/1445;
(Continued)

(56) References Cited

U.S. PATENT DOCUMENTS 5,170,800 A 12/1992 Smith et al.
5,431,674 A * 7/1995 Basile ................ A61B 18/1445
606/174
(Continued)

FOREIGN PATENT DOCUMENTS

CN 102204843 A 10/2011
CN 102427770 A 4/2012
(Continued)

OTHER PUBLICATIONS

English Translation; WO 2016068204 A1; Ishii (Year: 2016).*
(Continued)

*Primary Examiner* — Khadijeh A Vahdat
*Assistant Examiner* — Marina Delaney Templeton
(74) *Attorney, Agent, or Firm* — ArentFox Schiff LLP

(57) ABSTRACT

An electrosurgical resector tool having an energy delivery structure that provides a plurality of operational modalities that facilitate biological tissue cutting and sealing using radiofrequency (RF) electromagnetic (EM) energy and/or microwave EM energy. The tool comprises a static first blade element, and a pivotable second blade element that has a length commensurate with the first blade element whereby, in a closed position, it lies adjacent to a laterally facing surface of the first blade element. The blade elements constitute an energy delivery mechanisms that is compact (Continued)

enough to enable the tool to be insertable through an instrument channel of a surgical scoping device, such as an endoscope, gastroscope or bronchoscope.

26 Claims, 8 Drawing Sheets

(52) U.S. Cl.
CPC ............... *A61B 2018/00107* (2013.01); *A61B 2018/00166* (2013.01); *A61B 2018/00202* (2013.01); *A61B 2018/00577* (2013.01); *A61B 2018/00607* (2013.01); *A61B 2018/0063* (2013.01); *A61B 2018/00982* (2013.01); *A61B 2018/1415* (2013.01); *A61B 2018/145* (2013.01); *A61B 2018/1457* (2013.01); *A61B 2018/1467* (2013.01); *A61B 2018/1861* (2013.01); *A61B 2018/1876* (2013.01)

(58) Field of Classification Search
CPC ................. A61B 18/085; A61B 18/18; A61B 2018/00607; A61B 2018/00577; A61B 2018/00202; A61B 2018/0063; A61B 2018/1876; A61B 2018/1415; A61B 2018/1457; A61B 2018/1467; A61B 2018/00107; A61B 2018/145; A61B 2018/00601; A61B 2018/00083; A61B 2018/146; A61B 2018/1861; A61B 2018/1838
See application file for complete search history.

(56) References Cited

U.S. PATENT DOCUMENTS

| | | | | |
|---|---|---|---|---|
| 5,906,630 A * | 5/1999 | Anderhub | ............... | A61B 17/29 606/208 |
| 5,908,420 A * | 6/1999 | Parins | ................. | A61B 18/1445 606/174 |
| 6,193,718 B1 * | 2/2001 | Kortenbach | ........ | A61B 18/1445 606/50 |
| 6,464,701 B1 | 10/2002 | Hooven et al. | | |
| 9,585,718 B2 * | 3/2017 | Tani | ................... | A61B 18/1815 |
| 2013/0144284 A1 * | 6/2013 | Behnke, II | ......... | A61B 18/1815 606/33 |
| 2013/0274733 A1 * | 10/2013 | Hancock | ............ | A61B 18/1445 606/33 |
| 2015/0133928 A1 * | 5/2015 | Soni | .................... | A61B 18/1445 606/51 |
| 2015/0196353 A1 * | 7/2015 | Hancock | .............. | A61B 18/042 606/46 |
| 2016/0228186 A1 * | 8/2016 | Hancock | ............ | A61B 18/1815 |

FOREIGN PATENT DOCUMENTS

| | | | | |
|---|---|---|---|---|
| CN | 103717162 A | | 4/2014 | |
| CN | 105848605 A | * | 8/2016 | ............. A61B 17/29 |
| EP | 0 717 966 A1 | | 6/1996 | |
| EP | 0795301 A1 | | 9/1997 | |
| EP | 2 233 098 A1 | | 9/2010 | |
| EP | 2 520 243 A1 | | 11/2012 | |
| EP | 2007293 B1 | | 1/2013 | |
| EP | 2 716 247 A1 | | 4/2014 | |
| GB | 2487288 A | | 7/2012 | |
| GB | 2522340 B | * | 1/2016 | ............. A61B 17/29 |
| WO | WO-2015101787 A2 | * | 7/2015 | ........... A61B 18/042 |
| WO | WO-2016068204 A1 | * | 5/2016 | ......... A61B 1/00101 |
| WO | WO 2017/198671 A1 | | 11/2017 | |
| WO | WO 2018/178254 A1 | | 10/2018 | |

OTHER PUBLICATIONS

English Translation; CN105848605 (A); White et al. (Year: 2016).*
International Preliminary Report on Patentability issued from the International Preliminary Examining Authority in counterpart International Application No. PCT/EP2018/077880, mailed on Jan. 17, 2020.
International Search Report and Written Opinion, issued by International Searching Authority in corresponding International Application No. PCT/EP2018/077880, mailed on Jan. 25, 2019.
Search Report under Section 17(5), issued by the United Kingdom Intellectual Property Office in counterpart United Kingdom Application No. GB1716865.9, dated Mar. 5, 2018.
Written Opinion of the International Preliminary Examining Authority, issued by the International Preliminary Examining Authority in corresponding International Application No. PCT/EP2018/077880, mailed on Sep. 13, 2019.

* cited by examiner

ELECTROSURGICAL RESECTOR TOOL

CROSS-REFERENCE TO RELATED APPLICATIONS

This application is a National Stage entry of International Application No. PCT/EP2018/077880, filed on Oct. 12, 2018, which claims priority to British Patent Application No. 1716865.9, filed on Oct. 13, 2017. The disclosures of the priority applications are hereby incorporated in their entirety by reference.

FIELD OF THE INVENTION

The invention relates to an electrosurgical resector tool, for cutting, coagulating and ablating biological tissue. In particular the invention relates to an electrosurgical resector tool capable of delivering radiofrequency (RF) energy and/or microwave frequency energy for cutting biological tissue, haemostasis (i.e. sealing broken blood vessels by promoting coagulation of blood) and tissue ablation.

BACKGROUND TO THE INVENTION

Surgical resection is a means of removing sections of organs from within the human or animal body. The organs may be highly vascular. When tissue is cut (i.e. divided or transected), small blood vessels may be damaged or ruptured. Initial bleeding is followed by a coagulation cascade where the blood is turned into a clot in an attempt to plug the bleed. During an operation it is desirable for a patient to lose as little blood as possible, so various devices have been developed in an attempt to provide bleeding-free cutting. For endoscopic procedures, it is also undesirable for a bleed to occur and not to be dealt with expediently, since the flow of blood may obscure the operator's vision. Instead of a sharp blade, it is known to use RF energy to cut biological tissue. The method of cutting using RF energy operates using the principle that as an electric current passes through a tissue matrix (aided by the ionic cell contents), the impedance to electron flow across the tissue generates heat. When a pure sine wave is applied to the tissue matrix, enough heat is generated within the cells to vaporize the water content of the tissue. There is thus a huge rise in the internal cell pressure that cannot be controlled by the cell membrane, resulting in rupture of the cell. When this occurs over a large area, it can be seen that the tissue is transected.

The above procedure works elegantly in lean tissue, but it is less efficient in fatty tissue because there are fewer ionic constituents to aid the passage of electrons. This means that the energy required to vaporize the contents of the cells is much greater, since the latent heat of vaporization of fat is much greater than the latent heat of vaporization of water. RF coagulation operates by applying a less efficient waveform to the tissue, whereby instead of being vaporized, the cell contents are heated to around 65° C., drying out the tissue by desiccation and denaturing the proteins in the vessel walls. This denaturing acts as a stimulus to the coagulation cascade, so clotting is enhanced. At the same time the collagen in the wall is denatured, turning from a rod-shaped to a coil-shaped molecule, causing the vessel to contract and reduce in size, giving the clot an anchor point, and a smaller area to be plugged.

However, RF coagulation is less efficient when fatty tissue is present because the electrical effect is diminished. It can thus be very difficult to seal fatty bleeders. Instead of having clean white margins, the tissue has a blackened burned appearance.

SUMMARY OF THE INVENTION

At its most general the present invention provides an electrosurgical resector tool having an energy delivery structure that provides a plurality of operational modalities that facilitate biological tissue cutting and sealing using radiofrequency (RF) electromagnetic energy and/or microwave EM energy. In particular, the invention relates to combined actuation and energy delivery mechanisms that are compact enough to enable the tool to be insertable through an instrument channel of a surgical scoping device, such as an endoscope, gastroscope or bronchoscope. The device could also be used to perform laparoscopic or open surgery, i.e. the bloodless resection of a liver lobe with the abdominal cavity open.

In one example, the electrosurgical resector tool may comprise a pair of blade elements that provide a scissor-like mechanism that can provide three complimentary modalities: (i) a gliding RF-based cut when the blade elements are closed, (ii) a scissor-type cut performed on tissue grasped between the blade elements using a combination of RF energy and applied pressure, and (iii) a coagulation or vessel sealing operation performed on tissue grasped between the blade elements using a combination of microwave energy and applied pressure. Moreover, the RF and/or microwave energy may be supplied in any of these modalities at a power level sufficient to cause tissue ablation. By suitable configuration of a pair of electrodes on the blade elements, the supplied RF or microwave energy in each of these operational modalities can be focussed in the region required. The pair of electrodes may both on the same blade element, or there may be an electrode on each blade element.

According to the present invention, there is provided an electrosurgical resector tool comprising: a shaft defining a lumen; an energy conveying structure for carrying radiofrequency (RF) electromagnetic (EM) energy and microwave EM energy through the lumen of the shaft, wherein the energy conveying structure comprises a coaxial transmission line extending in a longitudinal direction through the lumen, and wherein the coaxial transmission line comprises an inner conductor separated from an outer conductor by a dielectric material; an instrument tip mounted at a distal end of the shaft, wherein the instrument tip comprises: a static portion comprising a first blade element, wherein the first blade element; and a movable portion comprising a second blade element, wherein the movable portion is movable relative to the static portion between a closed position in which the first blade element and second blade element lie alongside each other to an open position in which the second blade element is spaced from the first blade element by a gap for receiving biological tissue, and wherein the first blade element or the second blade element comprises a longitudinally extending planar dielectric body having a first electrode on a first laterally facing surface thereof; a second electrode spaced away from the first electrode and electrically isolated therefrom by at least the planar dielectric body; and an actuator for controlling relative movement between the movable portion and the static portion, wherein the second blade element has a length commensurate with the first blade element whereby, in the closed position, it lies adjacent to a second laterally facing surface of the longitudinally extending planar dielectric body opposite to the first laterally facing surface thereof, and wherein the inner conductor is connected to one of the first electrode and the second electrode and the outer conductor is connected to the other of the first electrode and the second electrode, whereby the first electrode and the second electrode are operable: as active and return electrodes for delivering RF energy conveyed from the energy conveying structure; and a microwave field emitting structure for delivering microwave energy conveyed from the energy conveying structure.

In this structure, the first and second blade elements may resemble a scissors-type closure mechanism. Thus, the second blade element may be arranged to slide past the first blade element during movement between the open position and closed position, e.g. to effect mechanical cutting through application of a shearing force. The movable portion may be movable relative to the static portion in a plane parallel to a plane defined by the planar dielectric body. Herein the term "static" may mean that fixed in relation to the distal end of the shaft when in use (i.e. when the second blade element is moved between the open and closed position).

The shaft may be flexible, e.g. suitable for bending or other steering to reach the treatment site. A flexible shaft may enable the device to be usable in a surgical scoping device such as an endoscope. In other examples, the shaft may be rigid, e.g. for use in open surgery or with a laparoscope.

The first electrode and second electrode may be disposed at the cutting interface. In one example, both electrodes are on the same blade element, which may be on either the movable portion or the static portion. For example, the second electrode may be located on the second laterally facing surface of the longitudinally extending planar dielectric body. This may assist in provide uniform energy delivery at the cutting interface. Where both electrodes are on one blade element, the other blade element may be electrically inert, e.g. made of plastic or other insulator.

In another example, the first electrode may be on one of the blade elements, and the second electrode on the other blade element. For example, the longitudinally extending planar dielectric body may be on the first blade element, and the second electrode may extend along a side of the second blade element.

The first and second electrodes may thus be disposed along each side of the cutting interface, with the planar dielectric body in between. In this arrangement RF EM energy applied to the electrodes flows preferentially between the first and second blade elements across the cutting interface. Similarly, if microwave EM energy is applied while the blade elements are open, a microwave field emitted by the electrodes has a much higher field strength within the gap between the blade elements than elsewhere.

When in the closed position, the second electrode is separated from the first electrode along much of its length by the planar dielectric body. If RF EM energy is applied in this position, the RF EM energy preferentially flows around a distal tip and side edge of the closed blade elements, which facilitates a RF-only gliding cut performed by sliding the instrument tip through tissue.

The movable portion and thus the second blade element may be formed from an insulator-coated conductive material. For example, the movable portion may be a cast piece of stainless steel having a ceramic (e.g. alumina spray), synthetic plastic (e.g. Bakelite) or diamond-like carbon (DLC) coating. The second electrode may be formed at a side portion of the second blade element where the insulator coating is removed. The second electrode may be the exposed conductive material of the movable portion, or may comprise an additional conductive layer (e.g. of gold or the like) deposited or otherwise affixed to the exposed conductive material.

The second blade element may comprise a laterally protruding flange along its side portion. The flange thus protrudes towards the first blade element when in the closed position. The second electrode may be formed on a laterally facing edge of the laterally protruding flange.

The static portion may comprise a support arm on which the movable portion is mounted. The support arm may form part of an electrical connection between the energy conveying structure and the second electrode. For example, the support arm may be formed from an insulator-coated conductive material, and may comprise a proximal contact portion at which the insulator coating is removed and which is electrically connected to the inner conductor or outer conductor of the coaxial transmission line. The support arm may have a proximal recess for attachment to a distal end of the coaxial transmission line. Other types of electrical connection may also be used. For example, a flexible conductor may be connected between the energy conveying structure (e.g. the inner conductor or outer conductor of the coaxial transmission line) and the first electrode or second electrode. Preferably the length of any flexible conductor is equal to or less than an eighth of a wavelength of the microwave energy, in order to prevent it from affecting the emitted field.

The coaxial transmission line may be adapted to convey both the RF EM energy and the microwave EM energy. Alternatively, the energy conveying structure may comprise different routes for the RF EM energy and microwave EM energy. For example, the microwave EM energy may be delivered through the coaxial transmission line, whereas the RF EM energy can be delivered via twisted pair wires or the like. Where a separate energy delivery route is provided, the first and second electrodes may comprise separate RF electrode portions and microwave electrode portions to enable the RF energy and microwave energy to be delivered from different regions of the instrument tip. For example, the microwave energy may be delivered from one of the blade elements, whereas the RF energy may be delivered between the blade elements.

The movable portion may be mounted to the support arm via a pivot connection. For example, the support arm may provide a clevis-type structure that supports a pivot axle on which the movable portion is mounted. The electrical connection between the energy conveying structure and the second electrode may pass through the pivot connection. For example, the pivot axle may be formed from a conductive material, and the insulator coating of the movable portion and the support arm may be removed where they respectively contact the pivot axle.

The dielectric material and inner conductor of the coaxial transmission line may extend beyond a distal end of the outer conductor. The inner conductor may include an exposed distal portion that is electrically connected to the first electrode, e.g. by directly overlapping with and contacting a proximal portion of the first electrode.

The movement between the movable portion and the static portion may be rotational or translational or a combination of the two. In one example, the movable portion may be pivotable relative to the static portion, whereby the second blade element is angled relative to the first blade element in the open position. This example may resemble a conventional scissor-type closure. The second blade element may be movable through an obtuse angle between the open position and the closed position. This may be useful for obtaining purchase on tissue to be grasped, especially tissue having a low surface profile.

In another example, it may be beneficial for a gap between the electrodes to be uniform once tissue is grasped therebetween, e.g. to ensure that the energy supplied is uniform along the length of the blade elements. In this example, the movable portion may be occupy a position in which the second blade element lies parallel to the first blade element but spaced therefrom to define a gap therebetween. The movable portion may by slidable from this position to the closed position, e.g. under operation of the actuator. The first blade element and the second blade element may then lie parallel in the longitudinal direction when sliding past one another. The spaced parallel position may be an intermediate position, e.g. from which the movable portion is pivotable to an angle with respect to the static portion.

The actuator may comprise a control rod slidably mounted in the flexible shaft. The control rod may have an attachment feature engaged with the movable portion, whereby longitudinal movement of the control rod in the shaft causes movement of the movable portion relative to the static portion. The attachment feature may be a hook or any suitable engagement for transmitting push and pull forces to the movable portion.

In one example, the movable portion comprises a cam surface against which the control rod acts to drive movement of the second blade element past the first blade element. The cam surface may be engagable only during a final stage of the closure operation, e.g. to provide an additional force boost to complete the closure. In one example, the cam surface may be provided by a slot in the movable portion. The attachment feature comprises an engagement portion for locating in the slot. A cam action may be provided by the engagement portion sliding along the slot.

The static portion may comprise a support arm that provide a mounting based (e.g. a pivot base) for the movable portion. The planar dielectric body may be a separate piece of material mounted on, e.g. adhered or otherwise affixed to, the support arm. The planar dielectric body may be formed from ceramic (e.g. alumina). Herein, reference to "planar" material may mean a flat piece of material having a thickness that is substantially less that its width and length. The planar dielectric body may have a length dimension aligned in the longitudinal direction, a thickness dimension aligned in a lateral direction, and a width dimension orthogonal to both the length and thickness dimensions. A plane of the planar dielectric body is that in which the length and width dimensions lie, i.e. a plane orthogonal to the width dimension.

The first electrode may be a conductive material (e.g. gold) deposited or otherwise mounted on the first laterally-facing surface of the planar dielectric body. The second laterally-facing surface of the planar dielectric body that faces in an opposite direction to the first laterally-facing surface may be exposed at the cutting interface.

The instrument tip may comprise a shield mounted around the static portion. The shield may comprise an insulting covering mounted around the static portion. For example, the insulating shield may cover the support arm of the static portion. The insulating shield may also be using to partly cover the first electrode, e.g. to ensure that an exposed portion of the first electrode has a desired shape for controlling the delivery or RF or microwave energy. The insulating covering may have one or more field-shielding conductive regions, e.g. patches of metallisation on its outer surface. These conductive regions may provide shielding for the electric fields, e.g. to prevent leakage of energy from the instrument in unwanted locations. The shield may moulded over the instrument tip following assembly. Alternatively, the shield may be formed from a tube of insulating material that can be cut (e.g. laser cut) to the desired shape and then mounted over the blade elements. The shield may be formed from a suitable insulating plastic, e.g. PEEK or the like. The material for the shield may preferably be resistant to high temperatures.

The first blade element may be shaped as a longitudinally extending finger having a upstanding tooth at its distalmost end. The second blade element may be shaped in a corresponding way, e.g. as an elongate finger having a downwardly extending tooth at its distalmost end. The distalmost teeth may assist in retaining tissue in the gap between the jaws as they are closed.

A longitudinally extending insert may be mounted in the lumen of the flexible shaft to prevent relative movement of the actuator or coaxial cable with the shaft from resulting in lost or jerky movement of the instrument tip. The insert may comprise a tubular body having a plurality of longitudinal sub-lumens formed therein, wherein each of the plurality of longitudinal sub-lumens breaks the outer surface of the tubular body. The tubular body is sized to fit snugly within the lumen so that its broken circumferential surface defines a plurality of feet that abut the inner surface of the shaft to resist relative movement therebetween.

The coaxial transmission line may comprise a coaxial cable mounted in a first sub-lumen of the tubular body. The actuator may comprise a control rod slidably mounted in a second sub-lumen of the tubular body. The control rod may have a low friction coating (e.g. of PTFE or the like) to facilitate longitudinal sliding relative to the insert. Alternatively, the second sub-lumen may have a low friction tube mounted therein, wherein the control rod can be slidably mounted in the low friction tube.

The instrument tip may be dimensioned to fit within an instrument channel of a surgical scoping device. Accordingly, in another aspect the invention provides an electrosurgical apparatus comprising: an electrosurgical generator for supplying radiofrequency (RF) electromagnetic (EM) energy and microwave EM energy; a surgical scoping device having an instrument cord for insertion into a patient's body, the instrument cord having an instrument channel extending therethrough; and an electrosurgical resector tool as described above inserted through the instrument channel of the surgical scoping device.

The apparatus may comprise a handpiece for controlling the electrosurgical resector tool. The handpiece may be mounted at a proximal end of the flexible shaft, e.g. outside the surgical scoping device. The handpiece may comprise: a body; an actuating element slidably mounted on the body; and a rotator rotatably mounted on the body. The coaxial transmission line and the flexible shaft of the electrosurgical resection tool may be mounted to slide relative to the body with the actuating element and rotate relative to the body with the rotator. The actuator of the electrosurgical resection tool may comprise a control rod extending through the lumen of the flexible shaft, wherein the control rod has a proximal portion that is mounted in a longitudinally fixed position relative to the body. With this arrangement, the actuating element is operable to control movement of the movable portion relative to the static portion, and the rotator is operable to control rotation of the electrosurgical resector tool relative to the instrument channel.

In use, the handpiece can deliver power to the electrosurgical resector tool at the distal end of the flexible shaft in combination with both a longitudinal (axial) force (via the control rod) and rotational force (via the flexible shaft). The longitudinal force may be used to control an end effector on the instrument, e.g. the movable portion discussed above, or a sliding blade or needle. The rotational force may be used to control the orientation of the instrument.

The connection between the components in the handpiece are such that the flexible shaft and the coaxial cable are slidably relative to the control rod. In other words, the position of the control rod can change relative to the flexible shaft, which can thus provide a physical movement at the distal end thereof for operating the instrument.

The body may be a barrel-type housing that lies on a axis that is aligned with the flexible shaft as it extends away from the body. A rotation axis of the rotator may be aligned with or coaxial within the axis of the body. The rotator may be a collar or ring mounted on an outer surface of the body. The rotator may be retained in a longitudinal (axial) direction on the body. For example, the body may have a circumferential recess in which the rotator is seated.

The control rod may be rotatable with respect to the body. This means that all of flexible shaft, control rod and coaxial cable rotate relative to the body upon rotation of the rotator. This can prevent twisting of components within the flexible shaft. In one example, the proximal portion of the control rod may be mounted on the rotator. If the rotator is axially fixed relative to the body, this attachment means that the control rod will rotate with the rotator but will not slide relative to the body. The proximal portion may include a radial extension that passes through the flexible shaft in order to connect to the rotator.

The handpiece may comprise an internal shaft that housing a proximal portion of the flexible shaft. The internal shaft may be coupled to the rotator to rotate with it. The internal shaft may be axially slidably along a track formed within the rotator.

The actuating element may comprise a shaft mounted to slide in a longitudinal direction (i.e. the axial direction mentioned above) within the housing. The actuating element and body may have grip elements, e.g. finger rings or the like, for a user to hold while operating the device.

The handpiece may comprise a power input port on the actuating element. The power input port may be a QMA connector or the like. The power input port may be connected to transfer power received therein to the coaxial cable. Thus, a proximal end of the coaxial cable may be connected to the actuating element to receive power from the power input port. The proximal end of the coaxial cable may be connected to the actuating element via a rotatable coupling to permit relative rotation therebetween.

The power input port may connect to an external coaxial cable e.g. from an electrosurgical generator. A connection direction into the power input port may extend perpendicularly to the direction in which the actuating element is slidable relative to the body. For example, the power input port may be at an underside of the actuating element.

The term "surgical scoping device" may be used herein to mean any surgical device provided with an insertion tube that is a rigid or flexible (e.g. steerable) conduit that is introduced into a patient's body during an invasive procedure. The insertion tube may include the instrument channel and an optical channel (e.g. for transmitting light to illuminate and/or capture images of a treatment site at the distal end of the insertion tube. The instrument channel may have a diameter suitable for receiving invasive surgical tools. The diameter of the instrument channel may be 5 mm or less.

Herein, the term "inner" means radially closer to the centre (e.g. axis) of the instrument channel and/or coaxial cable. The term "outer" means radially further from the centre (axis) of the instrument channel and/or coaxial cable.

The term "conductive" is used herein to mean electrically conductive, unless the context dictates otherwise.

Herein, the terms "proximal" and "distal" refer to the ends of the elongate probe. In use the proximal end is closer to a generator for providing the RF and/or microwave energy, whereas the distal end is further from the generator.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz, and most preferably 400 kHz.

BRIEF DESCRIPTION OF THE DRAWINGS

Embodiments of the invention are discussed in detail with reference to the accompanying drawings, in which.

DETAILED DESCRIPTION OF THE DRAWINGS

Figure 1:
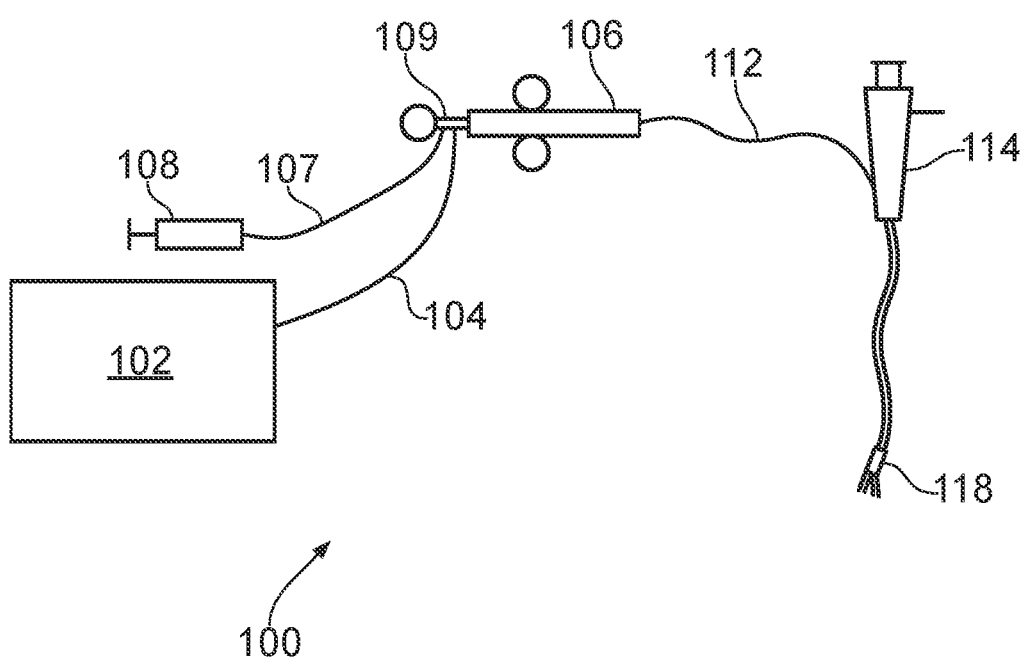
FIG. 1 is a schematic diagram of an electrosurgical system that is an embodiment of the invention.

FIG. 1 is a schematic diagram of a complete electrosurgical system 100 that is an embodiment of the invention. The system is arranged to treat (e.g. cut or seal) biological tissue using radiofrequency (RF) or microwave electromagnetic (EM) energy from an instrument tip. The system 100 comprises a generator 102 for controllably supplying the RF and microwave EM energy. A suitable generator for this purpose is described in WO 2012/076844, which is incorporated herein by reference. The generator 102 is connected to a handpiece 106 by an interface cable 104. The handpiece 106 may also be connected to receive a fluid supply 107 from a fluid delivery device 108, such as a syringe, although this is not essential. If needed, the handpiece 106 may house an instrument actuation mechanism that is operable by an actuator 109, e.g. a thumb operated slider or plunger. For example the instrument actuation mechanism may be used to operate a pivotable blade element of a resector instrument as discussed herein. Other mechanisms may also be included in the handpiece. For example, a needle movement mechanism may be provided (operable by a suitable trigger on the handpiece) for deploying a needle at the instrument. A function of the handpiece 106 is to combine the inputs from the generator 102, fluid delivery device 108 and instrument actuation mechanism, together with any other inputs which may be required, into a single flexible shaft 112, which extends from the distal end of the handpiece 106.

The flexible shaft 112 is insertable through the entire length of an instrument (working) channel of a surgical scoping device 114. The flexible shaft 112 has an instrument tip 118 that is shaped to pass through the instrument channel of the surgical scoping device 114 and protrude (e.g. inside the patient) at the distal end of the endoscope's insertion tube. The instrument tip 118 includes a pair of blade elements for gripping biological tissue and an energy delivery structure arranged to deliver RF or microwave EM energy conveyed from the generator 102. Optionally the instrument tip 118 may also include a retractable hypodermic needle for delivering fluid conveyed from the fluid delivery device 108. As described in more detail below, the handpiece 106 includes an actuation mechanism for opening and closing the blade elements of the instrument tip 118. The handpiece 106 also includes a rotation mechanism for rotating the instrument tip 118 relative to the instrument channel of the surgical scoping device 114.

The structure of the instrument tip 118 may be arranged to have a maximum outer diameter suitable for passing through the working channel. Typically, the diameter of a working channel in a surgical scoping device such as an endoscope is less than 4.0 mm, e.g. any one of 2.8 mm, 3.2 mm, 3.7 mm, 3.8 mm. The flexible shaft 112 may have a maximum diameter less than this, e.g. 2.65 mm. The length of the flexible shaft 112 can be equal to or greater than 1.2 m, e.g. 2 m or more. In other examples, the instrument tip 118 may be mounted at the distal end of the flexible shaft 112 after the shaft has been inserted through the working channel (and before the instrument cord is introduced into the patient). Alternatively, the flexible shaft 112 can be inserted into the working channel from the distal end before making its proximal connections. In these arrangements, the distal end assembly 118 can be permitted to have dimensions greater than the working channel of the surgical scoping device 114. The system described above is one way of introducing the instrument into a patient. Other techniques are possible. For example, the instrument may also be inserted using a catheter.

Although the examples herein are present in the context of a surgical scoping device, it is to be understood that the electrosurgical resector instrument may be embodiment in a device suitable for open surgery or use with a laparoscope.

Figure 2A:
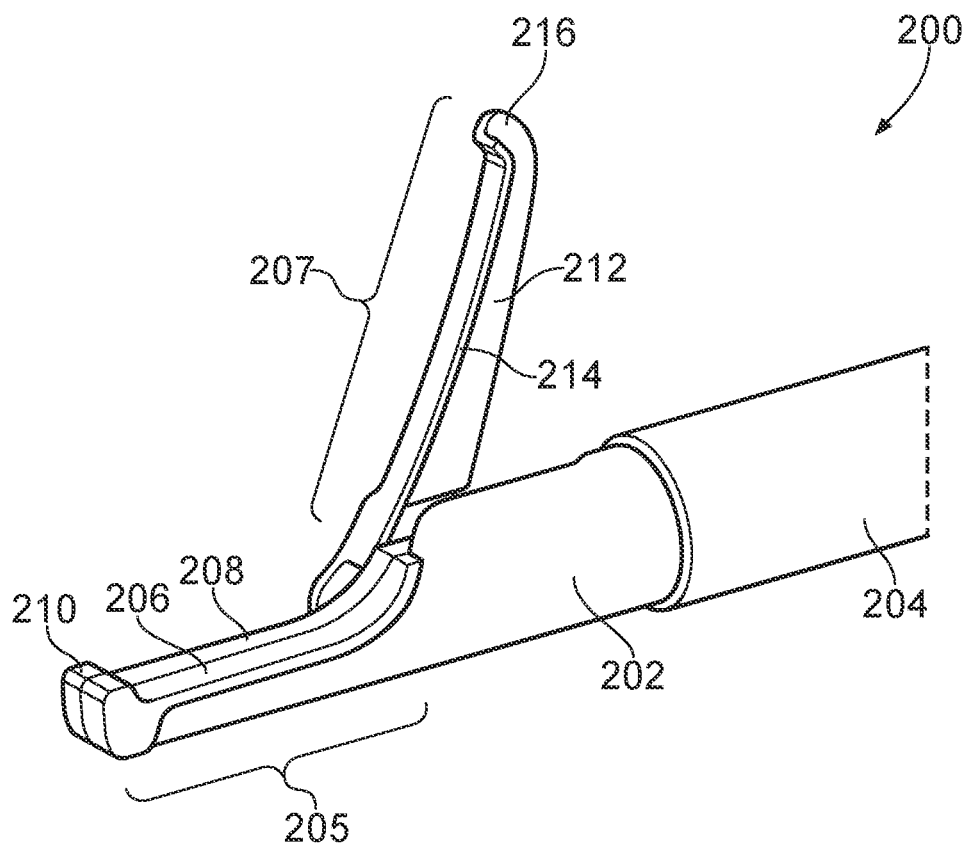
FIGS. 2A and 2B are perspective views of an instrument tip of an electrosurgical resector instrument that is an embodiment the invention in an open configuration and a closed configuration respectively.

FIG. 2A is perspective view of an instrument tip 200 of an electrosurgical resector instrument that is an embodiment the invention. The instrument tip 200 is mounted at the distal end of a flexible shaft 204, which may correspond to the flexible shaft 112 discussed above. In this embodiment, the instrument tip 200 comprises a static portion 202 that carries a first electrode 206, and a movable portion 212 that carries a second electrode 214. However, the invention need not be limited to this configuration. In other examples both electrodes may be provided on either the static portion 202 or the movable portion 212.

The static portion 202 has a proximal region that is secured to a distal end of the flexible shaft 204. The static portion 202 extends in a longitudinal direction away from the distal end of the flexible shaft 204. At its distal end, the static portion 202 defines a first blade element 205, which is a longitudinally extending finger having a upstanding tooth 210 at its distalmost end. The first electrode 206 extends along an upper surface of the first blade element 205.

The movable portion 212 is pivotably mounted on the static portion 202. In this embodiment, the movable portion 212 comprises a second blade element 207, which is an elongate finger having a length commensurate with the first blade element 205. The second blade element 207 has a downwardly extending tooth 216 at its distalmost end.

The movable portion is pivotable about a pivot axis located at a proximal end of the first blade element 205, whereby the second blade element 207 can swing between an open position (shown FIG. 2A) in which it is angled away from the first blade element 205 and a closed position (shown in FIG. 2B) where is lies alongside (i.e. laterally adjacent) to the first blade element 205. The range of movement of the movable portion may be such to allow the second blade element 207 to adopt an obtuse angle relative to the first blade element 205. This may be particular useful for grasping tissue that present a low surface profile.

The first blade element 205 and second blade element 207 may thus define a scissor-type closure mechanism in which tissue located in a gap between the blade elements 205, 207 when in the open position can have pressure applied to it as the second blade element 207 is moved to the closed position. The upstanding tooth 210 on the first blade element 205 and the downwardly extending tooth 216 on the second blade element 207 act to retain tissue in the gap as second blade element 207 moves to the closed position.

The first blade element 205 comprises a planar dielectric body 208, e.g. made from ceramic or other suitable electrically insulating material. The planar dielectric body 208 defines a plane that is parallel to a plane through which the second blade element 207 pivots. The planar dielectric body 208 provide an insulating barrier between the first electrode 206 and the second blade element 207. For example, the second blade element 207 is arranged to slide past a first surface of the planar dielectric body 208, and the first electrode 206 is formed on a second surface of the planar dielectric body 208, the second surface being on the opposite side of the planar dielectric body 208 from the first surface. The first electrode 206 may be made from a conductor exhibit high conductivity, e.g. gold or the like.

The second electrode 214 extends along a side surface of the second blade element 207 that slides past an adjacent side surface of the first blade element 205 (i.e. the first surface of the planar dielectric body 208 mentioned above) when the second blade element 207 is moved into the closed position. In this example, the second blade element 207 comprises a laterally protruding flange along a bottom edge thereof. The second electrode 214 extends along the laterally facing surface of the flange. The second blade element may be formed from an electrically conductive material that is coated with an insulating material. For example, it may be made from stainless steel with a ceramic or diamond-like carbon (DLC) coating. The insulating coating may be removed, e.g. etched away, from regions where it is not required. For example, the second electrode 214 may be formed by etching away the coating from the side edge of the lateral flange. A gold layer may be deposited over the etched surface to form the electrode. Other portions of the coating may be removed to enable an electrical connection to be made to the outer conductor of the coaxial cable, as explained below.

The flexible shaft 204 defines a lumen through which extends a coaxial cable (not shown) for conveying RF and microwave EM energy, and a longitudinally slidable control rod (shown in FIGS. 3A to 3D) for controlling movement of the movable portion 212.

As discussed in more detail with reference to FIG. 4, the first electrode 206 is electrically connected to an inner conductor of the coaxial cable and the second electrode 214 is electrically connected to an outer conductor of the coaxial cable. The instrument tip thus provides an energy delivery structure that is operable to deliver RF energy along a current path (e.g. through tissue) between the first electrode and second electrode, or microwave energy through a microwave field emitted by the first electrode and second electrode.

The instrument tip 200 may provide three operational modalities. In a first modality, the instrument can be used with the blade elements 205, 207 in the closed position to deliver RF EM energy to cut through biological tissue. In this first modality, the RF EM energy passes primarily between the first electrode 206 and second electrode 214 in a distal cutting zone 230 adjacent to the upstanding tooth 210 on the first blade element 205 and the downwardly extending tooth 216 on the second blade element 207. The instrument may thus be used to sweep or glide across or through tissue to effect cutting.

In a second modality, the blade elements 205, 207 may be used to perform a grasping cut, i.e. a cut through tissue captured between the blade elements. In this modality cutting is done by a combination of physical pressure applied by closing the blade elements 205, 207 and RF EM energy applied during the closing process.

In a third modality, the blade elements 205, 207 may be used to grasp and seal tissue, such as a blood vessel or the like. In this modality, microwave EM energy is delivered to the electrodes, which set up a microwave field that acts to coagulate the tissue held within the blade elements.

The static portion 202 may have a dielectric shield mounted over its outer surface. In this example, the dielectric shield is a thermoplastic polymer, e.g. polyether ether ketone (PEEK), or the like. The dielectric shield may be moulded over the device, or may be a cover (e.g. formed by laser cutting a suitably size tube) that can slide over the instrument tip when the blade elements are in the closed position. The dielectric shield can be used to control the shape of the first electrode 206, e.g. to ensure that the first electrode 206 is exposed substantially only at an upper surface of the first blade element 205. In turn this can ensure that the RF and microwave energy delivered from he electrodes is focussed into the desired region.

FIGS. 3A, 3B, 3C and 3D are perspective views of the instrument tip 200 that illustrate the closing operation. FIGS. 3A to 3D show the opposite side of the instrument tip 200 from FIGS. 2A and 2B. The dielectric shield is omitted in FIGS. 3A to 3D for clarity.

Figure 3A:
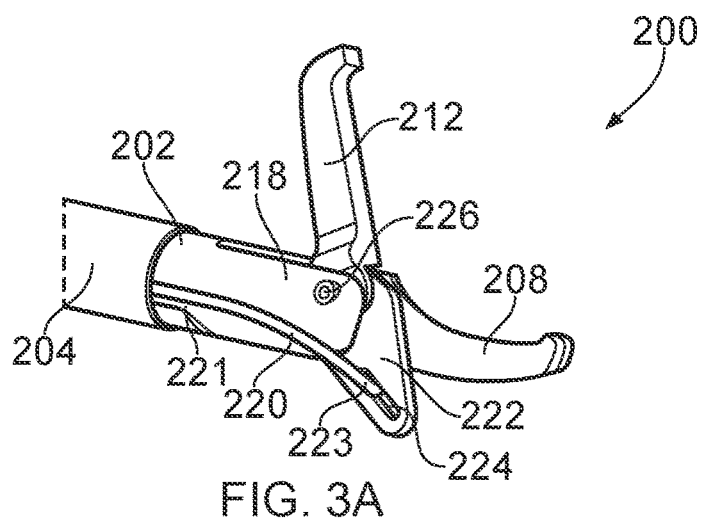
FIGS. 3A, 3B, 3C and 3D are perspective views of an instrument tip of an electrosurgical resector instrument illustrating various stages in a closing operation.

FIG. 3A illustrates the instrument tip 200 in an open position, with the movable portion 212 disposed so that the second blade element 207 is sits at an obtuse angle to the first blade element 205. As shown in FIG. 3A, the static portion 202 includes a longitudinally extending arm 218 that provides a pivot base to which the movable portion 212 is attached. The arm 218 has a pivot axle 226 rotatably mounted therein. The pivot axle 226 defines a laterally extending pivot axis (i.e. the pivot axis is orthogonal to the longitudinal direction defined by the flexible shaft 204).

A slidable control rod 220 protrudes from the flexible shaft 204. The static portion 202 has a guide channel 221 formed therein through which the control rod 220 passes. The control rod 220 has a distal attachment feature 223 that is engaged with the movable portion 212. In this example, the distal attachment feature 223 is a hook that engages a slot 224 formed in an attachment plate 222 of the movable portion 212. Other types of engagement may be used. Longitudinal sliding motion of the control rod 220 is transformed into pivoting motion of the attachment plate 222. The attachment plate 222 may be integrally formed with or otherwise operably coupled to the second blade element 207.

Figure 3B:
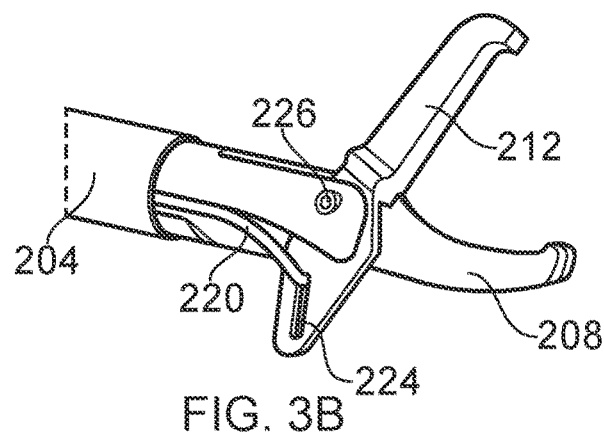

FIG. 3B shows the instrument tip 200 in a partly closed configuration, where the control rod 220 has been partly retracted into the flexible sleeve 204, and where there is an acute angle between the first and second blade elements.

Figure 3C:
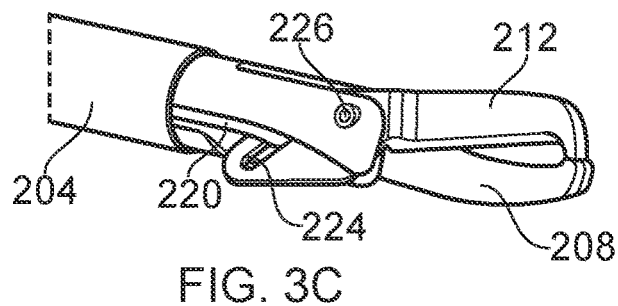
Figure 3D:
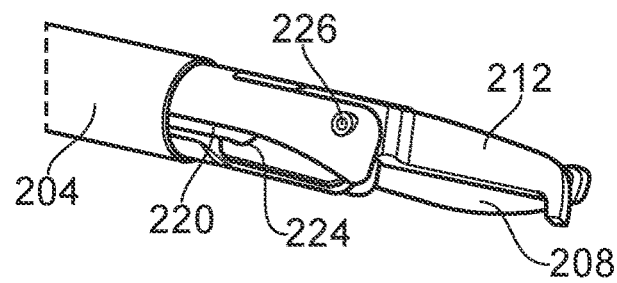

FIG. 3C shows the instrument tip 200 in another partly closed configuration, where the control rod 220 is further retracted into the flexible sleeve, and where the downwardly extending tooth 216 on the second blade element 207 is about to slide past the upstanding tooth 210 on the first blade element 205. In reaching this position, it can be seen that the distal attachment feature 223 of the control rod 220 has remained at a first end of the slot 224. The slot 224 provide a cam surface along which the control rod slides for the final portion of the closing operation, where the first and second blade elements slide past each other. FIG. 3D shows the final closed position, where the distal attachment feature 223 of the control rod 220 has moved to a second end of the slot 224. The slot advantageously provides a cam surface against which the distal attachment feature 223 acts in this final part of the movement operation, e.g. to boost the closure force to overcome resistance that can occur at the final stages of a cut.

Figure 4:
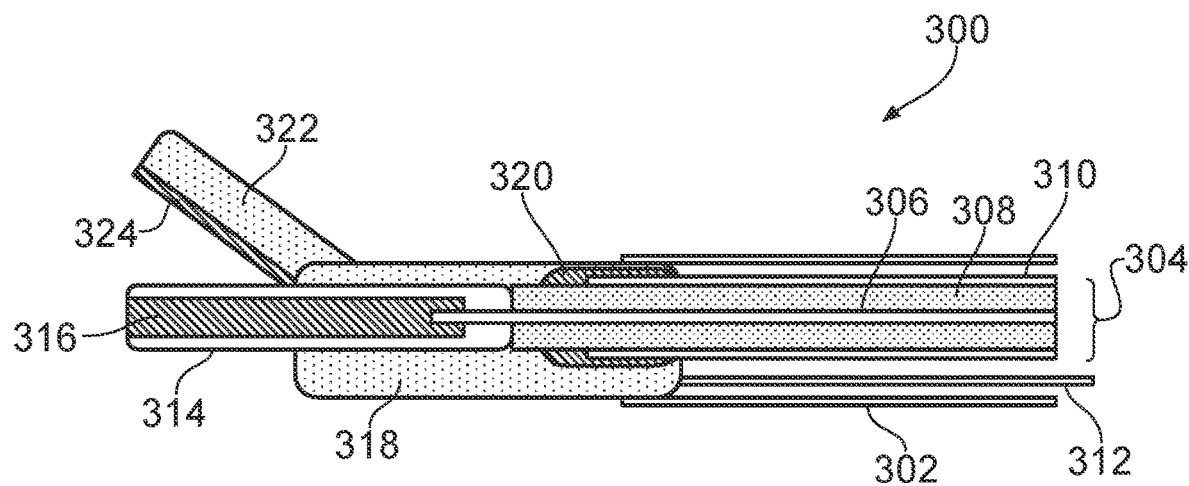
FIG. 4 is a schematic partially cut-away side view of an electrosurgical resector instrument that is an embodiment the invention.

FIG. 4 is a schematic partly cut-away side view of an instrument tip 300 for an electrosurgical resector instrument that is an embodiment of the invention. The instrument tip 300 is located at the distal end of a flexible sleeve 302, which conveys a coaxial cable 304 and a control rod 312. The control rod 312 is for controlling pivoting motion of a movable portion 322 relative to a static portion 318 in the same way as discussed above. The static portion 318 has a planar dielectric body 314 secured to it, e.g. by a suitable adhesive, the planar dielectric body 314 extending in a longitudinal direction away from the static portion 318 to form a first blade element. A first electrode 316 is formed on one side of the planar dielectric body 314.

The moveable portion 322 is pivotably mounted on the static portion 318 via a pivot axle (not visible in FIG. 4) at an opposite side of the planar dielectric body 314 to the first electrode 316. The moveable portion 322 comprises a second blade element that is arrange to slide past the first blade element in a similar manner to the first and second blade elements 205, 207 discussed above. The moveable portion 322 includes a second electrode 324 thereon that lies adjacent the opposite side of the planar dielectric body 314 when the blade elements are in a closed position.

The coaxial cable 304 comprises an inner conductor 306 that is separated from an outer conductor 310 by a dielectric material 308. The dielectric material 308 and inner conductor 306 extend beyond a distal end of the outer conductor 310. A distal end of the dielectric material 308 abuts a proximal end of the planar dielectric body 314. The inner conductor 306 extends distally from this junction to overlap with and electrically contact a proximal portion of the first electrode 316. The invention need not be limited to this arrangement. In other examples, the inner conductor may be electrically connected to an electrode on the movable portion, for example.

The static body 318 includes a support arm on which the movable portion is mounted. The planar dielectric body 314 may also be mounted on the support arm, e.g. using adhesive of the like. The support arm is formed from an electrically conductive material (e.g. stainless steel) with an electrically insulating coating. The coating is removed at a proximal contact portion 320 which is electrically connected to the outer conductor 310 of the coaxial cable 304. The movable portion 322 is also formed from an electrically conductive material (e.g. stainless steel) with an electrically insulating coating. The movable portion 322 is physically engaged with the static portion 318 at the pivot connection. An electrical connection between the second electrode 324 and the outer conductor 310 of the coaxial cable 304 passes through the pivot connection. For example, the pivot axle itself may be formed from an electrical conductive material (e.g. stainless steel). The insulating coating of the static portion 318 may be remove at a region of sliding engagement (e.g. an aperture or recess for receiving the pivot axle) between the static portion 318 and the movable portion 322. Similarly, the insulating coating of the movable portion 322 may be removed at this region. As the second electrode 324 may be or may be electrically connected to the electrically conductive material of the movable portion 322, a complete electrical connection to the outer conductor can be formed.

Figure 2B:
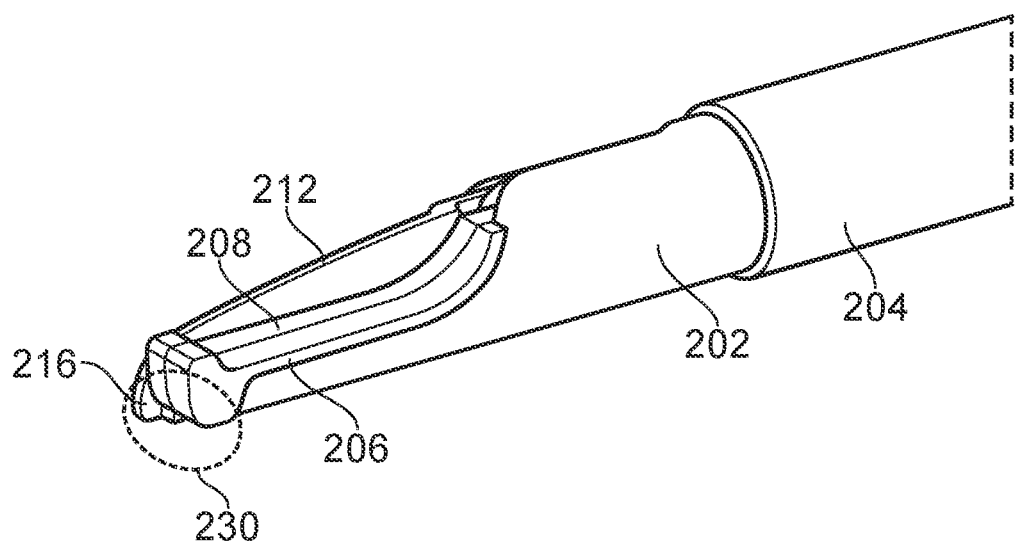
Figure 5:
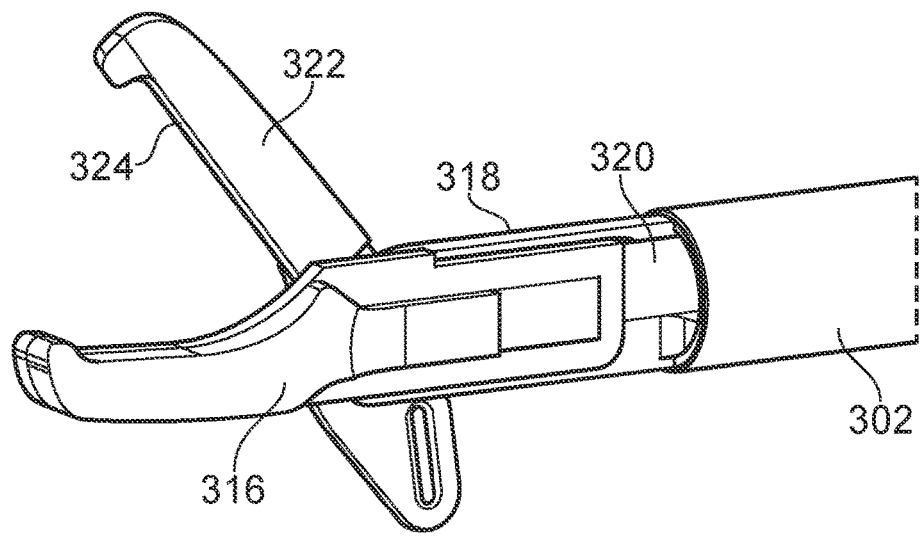
FIG. 5 is a partially cut-away perspective view of an electrosurgical resector instrument that is an embodiment the invention.

FIG. 5 is a partially cut-away perspective view of an electrosurgical resector instrument that illustrates how the schematic features of FIG. 4 may map on to a device similar to that shown in FIGS. 2A and 2B. Features in common with FIG. 4 are given the same reference numbers and are not described again.

Figure 6A:
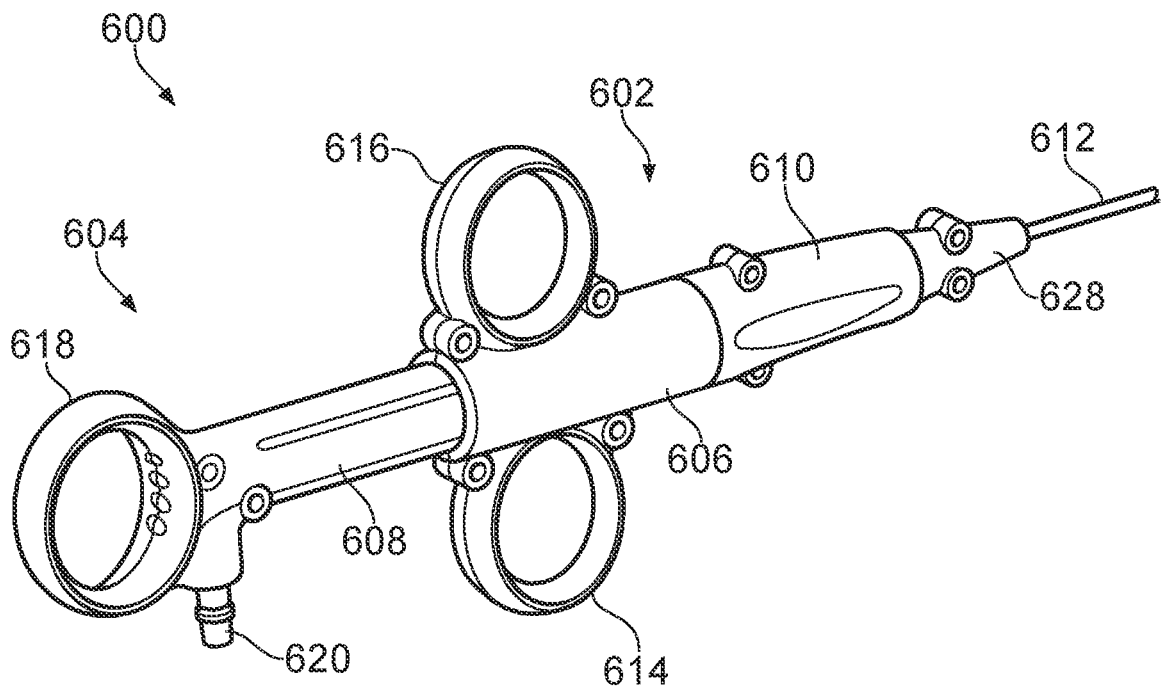
FIG. 6A is a perspective view of a handpiece of an electrosurgical apparatus that is an embodiment of the invention.

FIG. 6A is an illustration of a handpiece 600 which may be used as part of an electrosurgical apparatus that is an embodiment of the invention. The handpiece 600 includes a body 602 and an actuating portion 604. The body 602 includes a hollow barrel 606 in which a shaft 608 of the actuating portion 604 is slidably engaged. The body 602 also includes a rotator 610 which is rotatably connected to the barrel 606. The actuating portion 604 is connected to an internal shaft 628 which extends through the barrel 606 and rotator 610, and which protrudes from a distal end of the rotator 610. The internal shaft 628 moves longitudinally with the shaft 608, but is rotatable relative to it. An instrument shaft 612 exits the handpiece 600 from a distal end of the internal shaft 628. For example, the instrument shaft 612 may be flexible shaft 204 described above, which is connected to an instrument tip 200 at its distal end. The instrument shaft 612 is connected to rotate with the internal shaft 628.

The actuating portion 604 is slidable in a longitudinal direction relative to the body 602 along its shaft 608 between two positions: a closed position where a length of the shaft 608 is contained within the barrel 606, and an open position where the length of the shaft 608 is outside the barrel 606. FIG. 6A shows the handpiece 600 with the actuating portion 604 in the open position. The total range of motion of the actuating portion 604 relative to the body 602 may be approximately 35 mm. The longitudinal direction of motion of the actuating portion 604 relative to the body 602 is aligned with a longitudinal axis of the instrument shaft 612 as is passes out of the internal shaft 628. The shaft 608 may include one or more grooves 614 which engage with protrusions (not shown) inside the barrel 606, in order to prevent the actuating portion 604 from rotating relative to the body 602. The body 602 includes a pair of finger rings 614, 616 and the actuating portion 604 includes a thumb ring 618, which may be used to facilitate a user's grip when pushing and pulling the barrel 606 relative to the actuating portion 604. The actuating portion 604 further includes an input connector 620 for connecting an interface cable (e.g. interface cable 104) which connects the handpiece 600 to a generator (e.g. generator 102). The input connector 620 may for example be a QMA connector or any other suitable connector for interfacing with the generator.

Figure 6B:
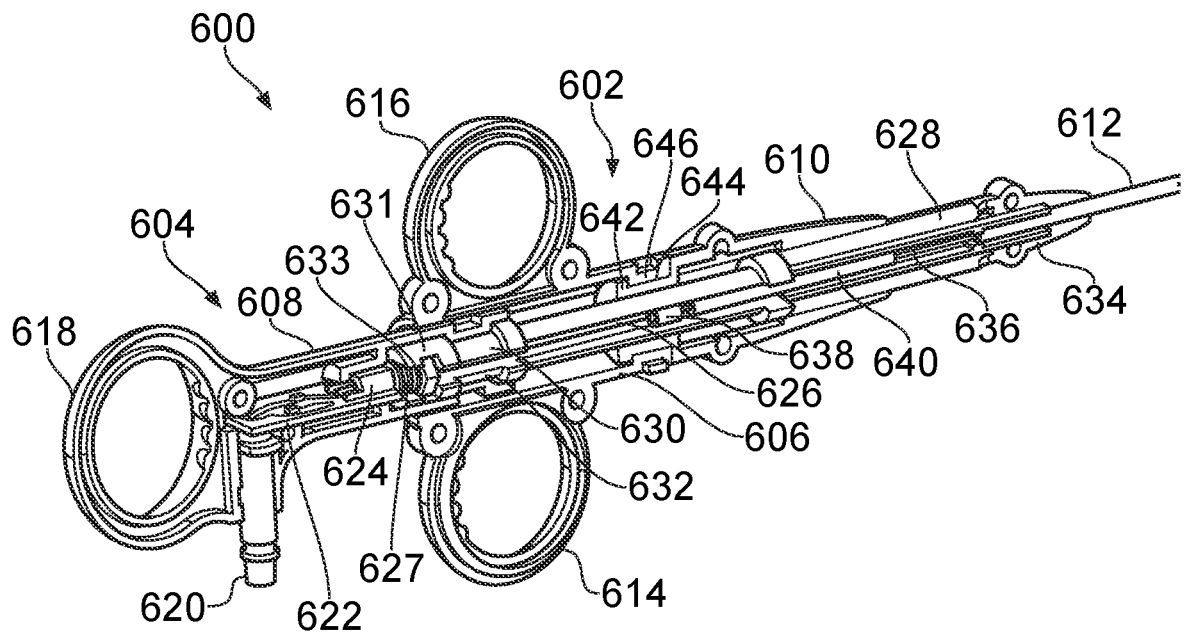
FIG. 6B is a part cutaway view of the handpiece of FIG. 6A, revealing parts of the internal structure of the handpiece.

FIG. 6B is a cut-away illustration of the handpiece 600, where certain parts are not shown in order to reveal the internal structure of the handpiece. Where features have already been described above in reference to FIG. 6A, identical reference numerals have been used.

The input connector 620 is electrically connected to a circuit board 622 contained within the shaft 608 of the actuating portion 604. The input connector 620 forms a substantially right angle with the circuit board 622, such that it is oriented along a direction which is substantially perpendicular to the direction of relative motion between the actuating portion and the body 602. In this manner, a cable which is connected to the input connector 620 may not get in a user's way. An output connector 624 is attached at an edge of the circuit board 622. The output connector 624 is electrically connected to a coaxial transmission line 626 via a mating connector 627 on the coaxial transmission line 626. The coaxial transmission 626 line runs through the handpiece 600 and enters the instrument shaft 612 at the distal end of the handpiece 600. The coaxial transmission line 626 may for example correspond to coaxial line 226 described above, which serves to convey RF and microwave EM energy to the instrument tip.

The electrical connection between the output connector 624 and the coaxial transmission line 626 is rotatable, i.e. it allows the coaxial transmission line to rotate about its axis relative to the output connector 624. Suitable connectors which enable rotatable electrical connections include QMA connectors, micro coaxial (MCX) connectors and microminiature coaxial (MMCX) connectors.

In other embodiments, the circuit board 622 may be omitted, and replaced by a single QMA to MCX right-angle connector.

As shown in FIG. 6B, the internal shaft 628 extends through and is longitudinally slidable relative to both the barrel 606 and the rotator 610 of the body 602. A distal end of the internal shaft 628 protrudes from the rotator 610. The length of the protruding portion depends on the position of the shaft 608 of the actuating portion 604. The internal shaft 628 is connected at a proximal end to the shaft 608 of the actuating portion 604, by means of a circumferential recess 630 around an outer surface of the internal shaft 628 which is engaged by a radial protrusion 632 on an inner surface of the shaft 608. The connection between the shaft 608 and the internal shaft 628 prevents the internal shaft 628 from moving longitudinally relative to the shaft 608, but allows the internal shaft 628 to rotate about its axis relative to the shaft 608. The internal shaft 628 may therefore be moved longitudinally backwards and forwards relative to the body 602 by moving the actuating portion 604 relative to the body 602.

The internal shaft 628 may include a proximal portion 631 having a cavity for holding the connector 627 of the coaxial transmission line 626 in position to ensure that it remains securely connected to the output connector 624 on the circuit board 622. Additionally, the connector 627 on the coaxial transmission line 626 may include a protrusion 633 which is configured to engage a slot in the proximal portion 630 of the internal shaft 628, to prevent the connector 627 from moving relative to the internal shaft 628. For example, the protrusion 633 may be a nut which is part of or attached (e.g. by soldering) to the connector 627. The protrusion 627 may also be configured to rotationally lock the connector 627 to the internal shaft 628, such that rotation of the internal shaft 628 causes the connector 627 to rotate.

The coaxial transmission line 626 passes through the internal shaft 628 where, at a distal end thereof, it enters the instrument shaft 612. A length of the instrument shaft 612 is contained within a distal portion 634 of the internal shaft 628, where it is fixed to the internal shaft 628. In this manner, both longitudinal and rotational motion of the internal shaft 628 may be transmitted to the instrument shaft 612. For example, the instrument shaft 612 may be glued using epoxy to the distal portion 634 of the internal shaft 628. Adhesion between the instrument shaft 612 and the internal shaft 628 may be improved by roughing the surface of the instrument shaft 612 before applying the epoxy. In some cases, the length of instrument shaft 612 contained in the distal portion 634 may be approximately 22 mm, to ensure good adhesion.

The rotator 610 is connected to the barrel 606 such that it is rotatable relative to the barrel about a longitudinal axis of the handpiece 600. In the example shown, the rotator 610 has a proximal portion 642 with a circumferential recessed channel 644 that receives a radially inwardly extending protrusion 646 on the barrel 606.

The internal shaft 628 passes through the rotator 610 and is engaged with the rotator 610 such that it is slidable relative to the rotator 610 along its length, but it is not rotatable relative to the rotator 610 (i.e. the rotator 610 and internal shaft 628 are rotationally locked relative to one another). This may be achieved by any kind of interengagement that transfers rotational movement. For example there may be one or more longitudinally oriented cooperating engagement elements (e.g. grooves and teeth) formed on an outer surface of the internal shaft 628 and an inner surface of the rotator 610. The engagement elements may respectively engage with each other to cause the internal shaft 628 to rotate as the rotator 610 is turned on the barrel 606. This in turn causes the instrument shaft 612, which is fixed to the internal shaft 628, to rotate such that an instrument tip connected at a distal end of the instrument shaft 612 may also be caused to rotate. However, as the internal shaft 628 is not rotationally coupled to the actuating portion 604, the actuating portion 604 is not caused to rotate by rotation of the rotator 610. The axis of rotation of the rotator 610 relative to the barrel 606 may be aligned with a longitudinal axis of the internal shaft 628, such that rotation of the rotator 610 causes rotation of the internal shaft 628 about its longitudinal axis.

A length of a main control rod 636 is contained within the internal shaft 628, and exits the handpiece through the instrument shaft 612. The main control rod 636 may be used to operate a movable portion (e.g. a pivotable blade element) on an instrument tip connected at a distal end of the instrument shaft 612. For example, main control rod 636 may correspond to main control rod 242 described above. A proximal end of the main control rod 636 is held fixed relative to the body 602 of the handpiece 600. Therefore, motion of the body 602 relative to the actuating portion 604 may cause the main control rod 636 to move longitudinally along the instrument shaft 612. This is because the longitudinal position of the instrument shaft 612 is held fixed relative to the actuating portion 604 (by means of the internal shaft 628, which is connected at one end to the actuating portion 604 and at another end to the instrument shaft 612), whilst the main control rod 636 is movable with the body 602 relative to the actuating portion 604, and thus the instrument shaft 612.

Thus, a user may move the actuating portion 604 relative to the body 602 in order to move the main control rod 636 backwards and forwards relative to the instrument shaft 612 and control the opening and closing of a movable portion (e.g. pivotable blade element) on an instrument tip connected at a distal end of the instrument shaft 612.

There are several possible ways for holding the proximal end of the main control rod 636 fixed relative to the body 602 of the handpiece 600. In the example shown, a block 638 is attached to the proximal end of the main control rod 636. The block 638 may for example be a piece of metal which is soldered or welded to the proximal end of the main control rod 638. The block 638 may be configured to fit in a holder (not shown) which is rigidly connected to the rotator 610, such that longitudinal motion of the body 602 relative to the actuating portion 604 is transmitted to the block 638 (and hence the main control rod 636) via the holder. The holder may be connected to the rotator 610 through an opening in a side wall of the internal shaft 628.

A portion of the main control rod 636 in the internal shaft 628 may be contained in a protective tube 640. The protective tube may be made of any suitable material (e.g. PTFE), and may serve to prevent the main control rod 636 from bending when the handpiece 600 is opened. Alternatively, a metal tube may be soldered or welded to the main control rod 636 to achieve the same effect.

The relative linear motion between the actuating portion 604 and the body 602 directly controls linear motion of the main control rod 636 relative to the instrument shaft 612. This may enable a user to accurately control the opening and closing of a pivotable blade element on an instrument tip at the distal end of the instrument shaft 612. Furthermore, the configuration of the handpiece 600 enables a user to comfortably hold the handpiece 600 in one hand and control the opening and closing of the blade element with one hand (by placing fingers of one hand in the finger rings 614, 616, 618). The user may also simultaneously rotate the rotator 610 with the other hand, in order to rotate the instrument tip. The orientation of the input connector 620 may ensure that any cable connected to the input connector 620 does not interfere with a user's operation of the handpiece 600. In this manner, the user isn't forced to hold the handpiece 600 in an awkward position in order to accommodate a cable, which might cause stress on the user's wrist.

In one example, a heat shrink or other stiffening material may be applied around a proximal portion of the instrument shaft 612. The length of this stiffening portion is selected to occupy a part of the shaft that will always be outside the insertion tube of the endoscope, even when the shaft is fully inserted. The stiffening portion may assist in translating torque from this part of shaft into the part that is within the insertion tube of the scoping device. It can also prevent the instrument shaft from rippling under actuation as well as under rotation. Moreover, it can give the clinician (i.e. scoping device operator) something larger in diameter to grip onto for both rotation and push/pull without having to communicate to the assistant.

The fact that the handpiece 600 has a free moving rotating joint in it permits the clinician to rotate without the assistant who will be holding the hand-piece, but also enables the assistant to apply rotation through the hand-piece if necessary.

Figure 7A:
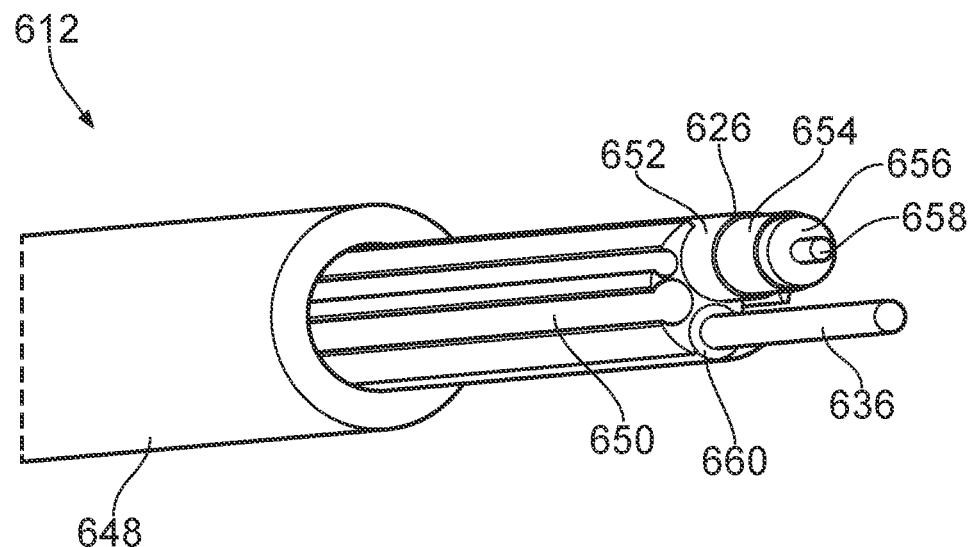
FIG. 7A is a perspective view of the contents of an instrument shaft that can be used with an electrosurgical resector instrument that is an embodiment of the invention.
Figure 7B:
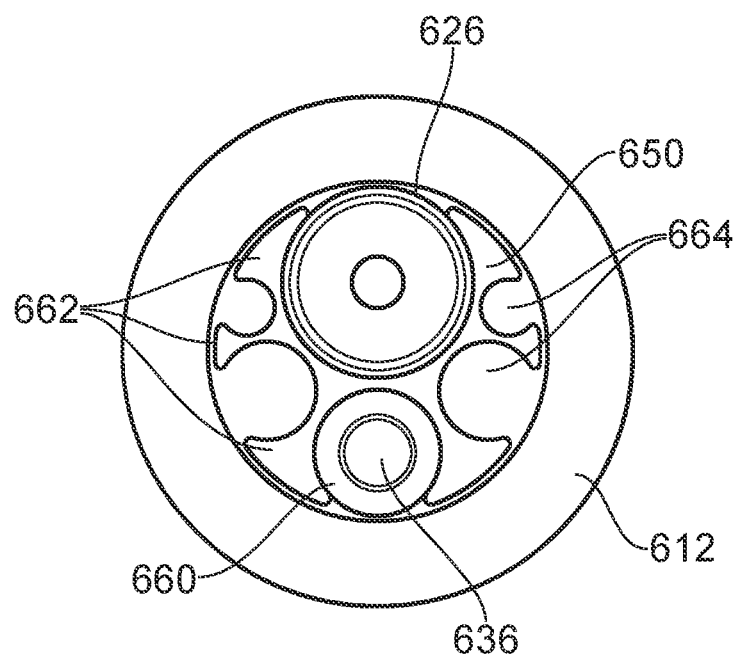
FIG. 7B is a cross-section of the instrument shaft shown in FIG. 7A.

FIG. 7A is a cut-away perspective view of the instrument shaft 612 as it travels towards the instrument tip. The instrument shaft 612 comprises a outer sleeve 648 that defines a lumen for conveying the coaxial cable 626 and control rod 636. In this example, the coaxial cable 626 and control rod 636 are retained in a longitudinally extending insert 650. The insert 650 is an extrusion, e.g. formed from a deformable polymer such as PEEK or other plastic with similar mechanical properties. As shown more clearly in FIG. 7B, the insert 650 is a cylindrical element having a series of sub-lumens 664 cut away around its outer surface. The sub-lumens 664 break through the outer surface of the insert 650 to define a plurality of discrete feet 662 around the circumference thereof. The sub-lumens 664 can be sized to convey components such as the coaxial cable 626 or control rod 636, or may be for the purpose of allowing fluid flow along the lumen of the sleeve 648.

It may be beneficial for the insert not to include any enclosed sub-lumens. Fully enclosed sub-lumens can be prone to retaining deformations if stored in a bent condition. Such deformations can lead to jerky motion in use.

The insert 650 may comprise a sub-lumen for receiving the coaxial cable 626. In this example, the coaxial cable 626 comprises an inner conductor 658 separated from an outer conductor 654 by a dielectric material 656. The outer conductor 654 may in turn have a protective cover or sheath 652, e.g. formed from PTFE or other suitably low friction material to permit relative longitudinal movement between the insert and coaxial cable as the shaft with flexing of the shaft.

Another sub-lumen may be arranged to receive a standard PFTE tube 660 through which the control rod 636 extends. In an alternative embodiment, the control rod 636 may be provided with a low-friction (e.g. PFTE) coating before use, so that a separate PFTE tube is not required.

The insert is arranged to fill, i.e. fit snugly within, the lumen of the sleeve 648 when mounted with the coaxial cable 626 and control rod 636. This means that the insert functions to restrict relative movement between the coaxial cable, control rod and sleeve during bending and rotation of the shaft 612. Moreover, by filling the sleeve 648, the insert helps to prevent the sleeve from collapsing and losing rotation if rotated excessively. The insert is preferably made from a material that exhibits rigidity to resist such movement.

The presence of the insert may furthermore prevent "lost" travel of the control rod caused by deformation of the instrument shaft 612. Such lost travel can occur in the absence of the insert for two reasons.

Firstly, the control rod 636 can move from side to side in the sleeve 648 so that when the sleeve follows a curved path it is able to go round the outside of bends which is a longer path than the length of the centre-line which is also the length of the sleeve when straight. For example, if an inside diameter of the sleeve was 2.15 mm, and a diameter of the control rod 0.4 mm, the centre-line of the control rod may be as much as 0.875 mm away from the centre-line of the sleeve. In each 180 degrees of bend, if the control rod goes to the outer limit of its possible travel within the sleeve, the path of the control rod would be 2.75 mm longer than the length along the centre-line of the sleeve. Thus, five 180 degree bends could yield 13.75 mm 'lost' travel.

Secondly, the control rod 636 may follow a sinuous path inside the sleeve 648, even if the sleeve is straight, which is longer than the length of the sleeve. Thus, in any location where the control rod is unsupported, it may bow sideways. The bowed shape would be like a sine wave. If it was stopped from going very far sideways, then it might have multiple bows down its length. Within the sleeve, the control rod cannot bow sideways but has to wrap round the inside of the sleeve, with its centre at a radius of 0.875 mm from the sleeve centre. Each wrap round the tube is equivalent to 5.5 mm of bowing. The length increase of a sinusoidal path over a direct path is calculated with an elliptic integral. For small ratios of a bow (a) to the straight length (p) of two bows, the change in length is close to that for the arc of a circle, and for this the ratio of the lengths is 8a/p sin(8a/p), and the difference (lost travel) is approximately 8a/p sin(8a/p−1≈(8a/p²/6). For instance, if the actuator rod had 6 loops (3 in each direction) down a 2.3 m length, and each one went twice round the centre-line, then p=2300/3=766.666 mm, and a=11 mm, and the lost travel is 0.22%, or 5 mm.

The extruded insert discussed above provides cam-like feet that jam on the inside of the sleeve and impede the wrapping of the control rod around the axis of the sleeve. This will reduce the lost travel discussed above.

Figure 8A:
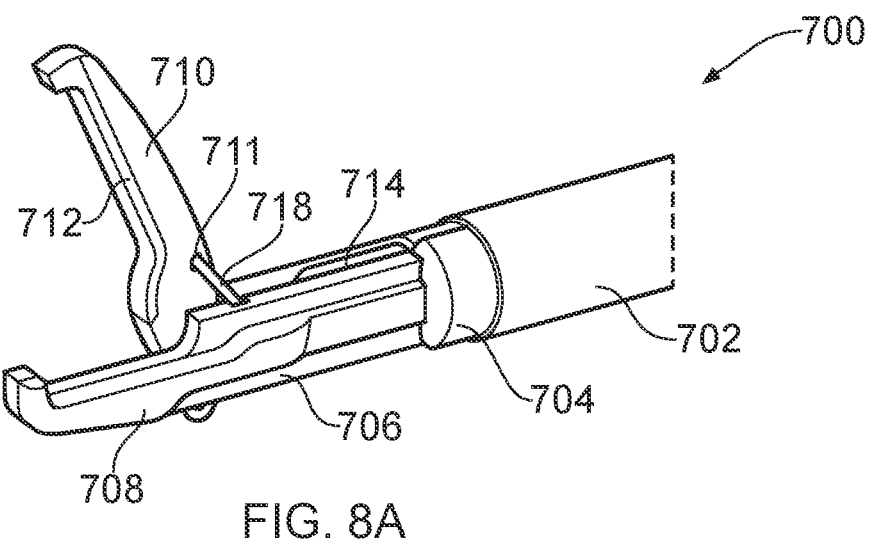
FIGS. 8A, 8B and 8C are perspective views of an instrument tip of an electrosurgical resector instrument that is another embodiment of the invention.
Figure 8B:
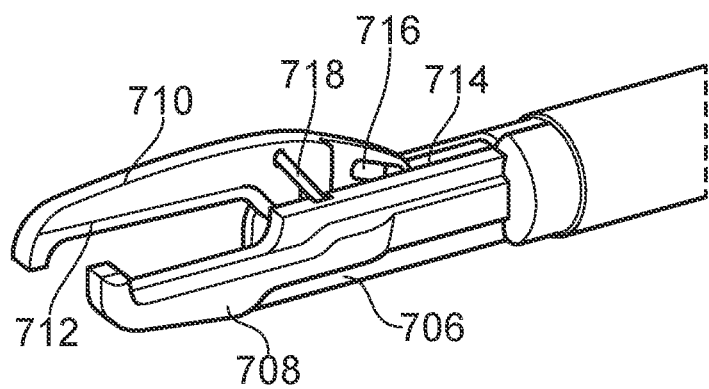
Figure 8C:
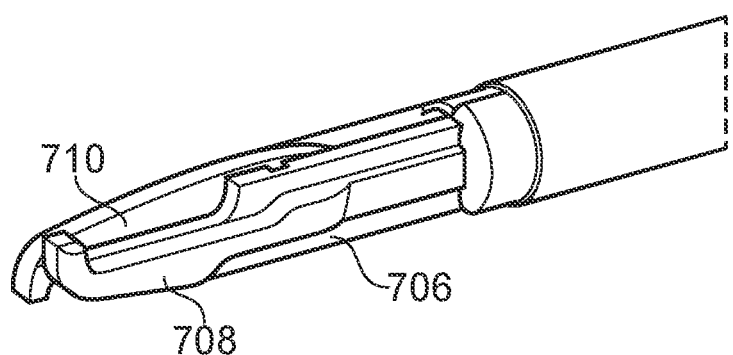

FIGS. 8A, 8B and 8C are perspective views of an instrument tip 700 of an electrosurgical resector instrument that is another embodiment of the invention. In this arrangement, the instrument tip is modified to provide a parallel closing action between the blade elements, as opposed to the pivoting scissor-type action discussed above.

Similarly to the instrument tip 200 discussed above, the instrument tip 700 comprises a static portion 706 that carries a first electrode 708, and a movable portion 710 that carries a second electrode 712. The instrument tip 700 is mounted at the distal end of a flexible shaft 702. A shielding element 704 is mounted over a junction between a coaxial cable conveyed by the shaft 702 and a proximal end of the first electrode 706.

The static portion 706 has a proximal region that is secured to a distal end of the flexible shaft 702. The static portion 706 extends in a longitudinal direction away from the distal end of the flexible shaft 702 and defines a first blade element in a distal region. The first blade element is a longitudinally extending finger having a upstanding tooth at its distalmost end. The first electrode 708 extends along an upper and side surfaces of the first blade element.

The movable portion 710 is pivotably mounted on the static portion 706. In this embodiment, the movable portion 710 comprises a second blade element, which is an elongate finger having a length commensurate with the first blade element. The second blade element has a downwardly extending tooth at its distalmost end.

In this example, the movable portion 710 is pivotable about a pivot axis 711 that is itself movable relative to the static portion 706. Similar to the structure discussed above, the instrument tip 700 comprises a control rod 714 that is slidable mounted in the shaft 702 and which engages a slot 716 on a proximal part of the movable portion 710. The movable portion 710 is connected to the static portion 706 by a connector rod 718. A first end of the connector rod 718 is pivotably connected to the movable portion 710 at the pivot axis 711, and a second end of the connector rod 718 is slidably mounted to the static portion 706 in a channel (not shown) formed therein.

FIG. 8A shows the instrument tip 700 in an open configuration, where the control rod 714 is extended out of the shaft 702 to push connector rod 718 into a deployed position where the pivot axis 711 is moved away from the static portion and the movable portion is pivoted around the pivot axis 711 so that the second blade element is at an angle to the first blade element.

FIG. 8B shows the instrument tip 700 in an intermediate configuration, wherein the control rod 714 is partly retracted so that the connector rod 718 remains in the deployed position where the pivot axis 711 is spaced away from the static portion 706, but where the movable portion has pivoted around the pivot axis so that the second blade element is parallel to the first blade element.

FIG. 8C shows the instrument tip 700 in a closed configuration, wherein the control rod 714 is fully retracted to cause the connector rod 718 to move to a withdrawn position where the pivot axis 711 is drawn into the static portion 706 so that the second blade element passes alongside the first blade element while remaining parallel therewith.

Figure 9A:
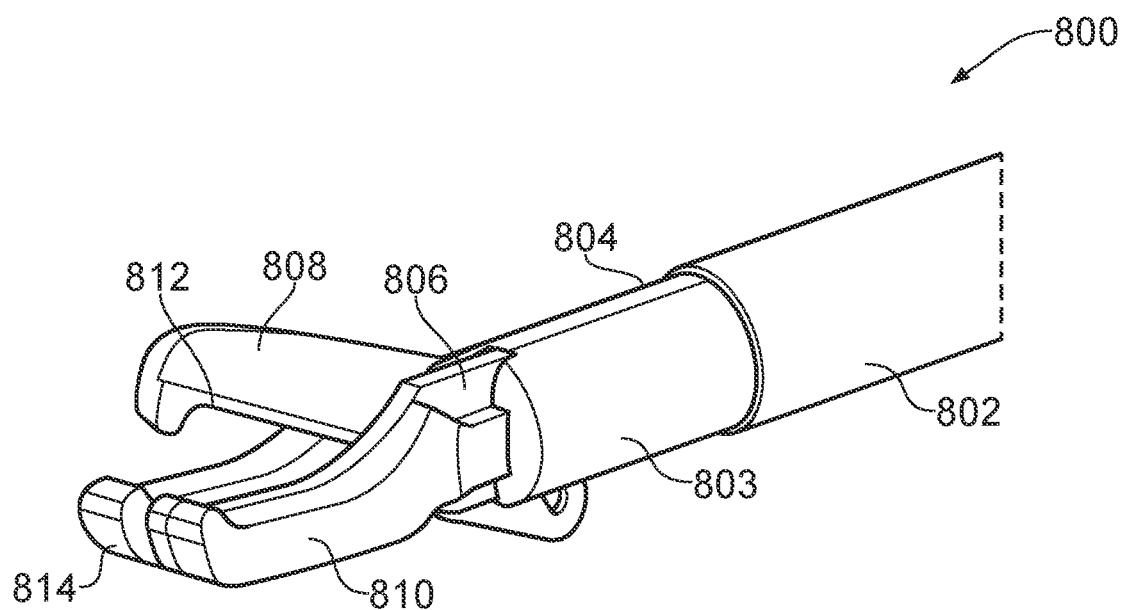
FIGS. 9A and 9B are perspective views of an instrument tip of an electrosurgical resector instrument that is yet another embodiment of the invention.
Figure 9B:
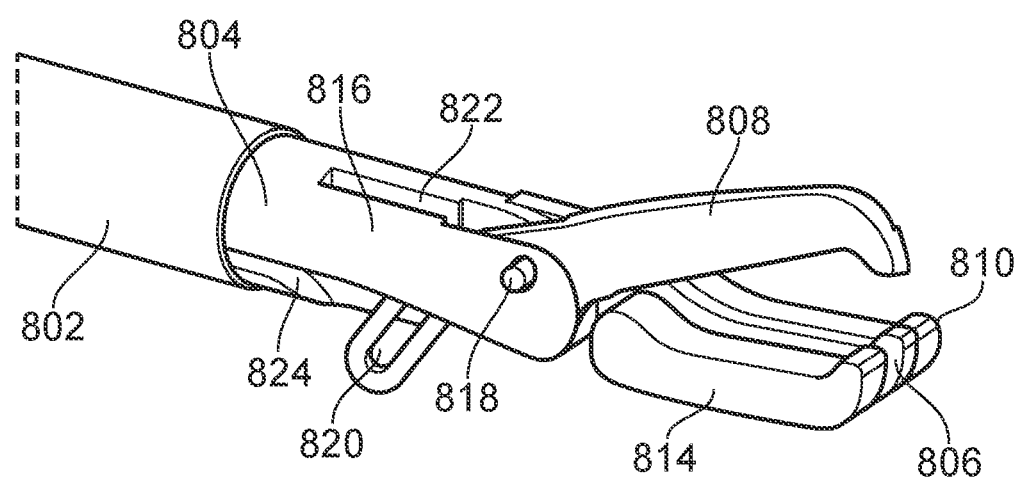

FIGS. 9A and 9B are perspective views of an instrument tip 800 of an electrosurgical resector instrument that is another embodiment of the invention. In this arrangement, the instrument tip is modified to provide a wider base to create better tissue sealing capabilities by confining or concentrating the microwave field set up between the electrodes.

Similarly to the instrument tip 200 discussed above, the instrument tip 800 comprises a static portion 804 that comprises a planar dielectric body 806 having a first electrode 810 thereon, and a movable portion 808 that carries a second electrode 812. The instrument tip 800 is mounted at the distal end of a flexible shaft 802. A shielding element 803 is mounted over a junction between a coaxial cable conveyed by the shaft 802 and a proximal end of the first electrode 810.

The static portion 804 has a proximal region that is secured to a distal end of the flexible shaft 802. The planar dielectric body 806 extends in a longitudinal direction away from the distal end of the flexible shaft 802 and defines a first blade element in a distal region. The first blade element is a longitudinally extending finger having a upstanding tooth at its distalmost end. The first electrode 810 extends along an upper and side surfaces of the first blade element.

The movable portion 808 is pivotably mounted on the static portion 804. In this embodiment, the movable portion 808 comprises a second blade element, which is an elongate finger having a length commensurate with the first blade element. The second blade element has a downwardly extending tooth at its distalmost end. The second electrode 812 extends along a side edge of the second blade element.

In this example, the static portion 804 comprise a third electrode 814. The third electrode 814 is formed from a conductive material and takes the form of a third blade element having the same shape as the first blade element, but spaced laterally from it on the opposite side of the planar dielectric body 806 to the first electrode 810. The third electrode 814 is spaced from the first blade element by a gap that is sized to receive the second blade element as is pivoted from an open position to a closed position in the same way as described above with reference to FIGS. 2A and 2B.

FIG. 9B shows the opposite side of the instrument tip 800. The static portion 804 comprises a longitudinal arm 816 that supports a pivot axle 818 on which the movable portion 808 is mounted. A channel 822 is cut or otherwise formed in the static portion 804 to receive the movable portion 808 as it moves into the closed position.

Pivoting of the movable portion is controlled by a longitudinally retractable control rod (not shown in FIG. 9B) that extends from the shaft 802 via guide channel 824 to engage with a slot 820 formed in the movable portion 808, in a similar manner as described above with reference to FIGS. 3A to 3D.

The third electrode 814 may be electrically connected to the first electrode 810 by a laterally extending conductive portion, e.g. pin or rod, (not shown) that passes across the gap between the third electrode 814 and the first blade element beneath the second blade element.

With the structure shown in FIGS. 9A and 9B, the instrument tip can support a wider extent of tissue to be gripped between the blade elements. Moreover, the microwave field created between the second electrode 812 and the first and third electrodes 810, 814 may exhibit a more consistent effect on gripped tissue on both sides of the second blade element. In this example it may be desirable for the inner conductor of the coaxial transmission line to be connected to the second electrode and the outer conductor to the first and third electrodes, whereby the first and third electrodes perform a field shielding function as the second blade element is moved to the closed position.

The invention claimed is:

1. An electrosurgical resector tool comprising:
 a shaft defining a lumen;
 an energy conveying structure for carrying radiofrequency (RF) electromagnetic (EM) energy and microwave EM energy through the lumen of the shaft, wherein the energy conveying structure comprises a coaxial transmission line extending in a longitudinal direction through the lumen, and wherein the coaxial transmission line comprises an inner conductor separated from an outer conductor by a dielectric material;
 an instrument tip mounted at a distal end of the shaft, wherein the instrument tip comprises:
  a static portion comprising a first blade element, wherein the first blade element comprises a longitudinally extending planar dielectric body having a first electrode on a first laterally facing surface thereof, wherein the longitudinally extending planar dielectric body comprises a second laterally facing surface opposite the first laterally facing surface thereof;
  a movable portion comprising a second blade element, wherein the movable portion is pivotable relative to the static portion within a rotation plane between a closed position in which the first blade element and second blade element lie alongside each other in a lateral direction that is normal to the rotation plane to an open position in which the second blade element is spaced from the first blade element by a gap for receiving biological tissue;
  a second electrode located on the movable portion, whereby the second electrode is spaced away from the first electrode and electrically isolated therefrom by the longitudinally extending planar dielectric body when the movable portion is in the closed position; and
  an actuator for controlling relative movement between the movable portion and the static portion,
 wherein the second blade element has a length commensurate with the first blade element whereby, in the closed position, it lies adjacent to the second laterally facing surface of the longitudinally extending planar dielectric body,
 wherein the longitudinally extending planar dielectric body has a length commensurate with the first and second blade elements, thereby isolating the first and second electrodes from each other along their length when in the closed position, and wherein the inner conductor is connected to one of the first electrode and the second electrode and the outer conductor is connected to the other of the first electrode and the second electrode, whereby the first electrode and the second electrode are operable:

as active and return electrodes for delivering RF energy conveyed from the energy conveying structure to cut biological tissue grasped between the blade elements; and a microwave field emitting structure for delivering microwave energy conveyed from the energy conveying structure to coagulate biological tissue grasped between the blade elements; and wherein the first blade element is shaped as a longitudinally extending finger having an upstanding tooth at its distalmost end, and wherein the second blade element is shaped as an elongate finger having a downwardly extending tooth at its distalmost end.

2. The electrosurgical resector tool according to claim 1, wherein the static portion comprises a support arm on which the movable portion is mounted, the support arm forming part of an electrical connection between the energy conveying structure and the second electrode.

3. The electrosurgical resector tool according to claim 2, wherein the support arm is formed from an insulator-coated conductive material, and wherein the support arm comprises a proximal contact portion at which an insulator coating is removed to form part of the electrical connection between the energy conveying structure and the second electrode.

4. The electrosurgical resector tool according to claim 2, wherein the electrical connection between the energy conveying structure and the second electrode connects the outer conductor of the coaxial transmission line to the second electrode.

5. The electrosurgical resector tool according to claim 2, wherein the dielectric material and inner conductor of the coaxial transmission line extend beyond a distal end of the outer conductor, and wherein the inner conductor includes an exposed distal portion that is electrically connected to the first electrode.

6. The electrosurgical resector tool according to claim 2, wherein the movable portion is mounted to the support arm via a pivot connection, and wherein the electrical connection between the energy conveying structure and the second electrode passes through the pivot connection.

7. The electrosurgical resector tool according to claim 1, wherein the rotation plane is parallel to a plane defined by the planar dielectric body.

8. The electrosurgical resector tool according to claim 1, wherein the second blade element is arranged to slide past the first blade element during movement between the open position and closed position.

9. The electrosurgical resector tool according to claim 8, wherein the first blade element and the second blade element lie parallel in the longitudinal direction when sliding past one another.

10. The electrosurgical resector tool according to claim 1, wherein the second blade element is angled relative to the first blade element in the open position.

11. The electrosurgical resector tool according to claim 1, wherein the second blade element is movable through an obtuse angle between the open position and the closed position.

12. The electrosurgical resector tool according to claim 1, wherein the actuator comprises a control rod slidably mounted in the shaft, the control rod having an attachment feature engaged with the movable portion, whereby longitudinal movement of the control rod in the shaft causes movement of the movable portion relative to the static portion.

13. The electrosurgical resector tool according to claim 12, wherein the movable portion comprises a cam surface against which the control rods acts to drive movement of the second blade element past the first blade element.

14. The electrosurgical resector tool according to claim 13, wherein the cam surface is provided by a slot in the movable portion, and wherein the attachment feature comprises an engagement portion for locating in the slot.

15. The electrosurgical resector tool according to claim 1, wherein the instrument tip comprises a shield mounted around the static portion.

16. The electrosurgical resector tool according to claim 15, wherein the shield comprises an insulating covering mounted around the static portion, wherein the insulating covering has one or more field-shielding conductive regions on its outer surface.

17. The electrosurgical resector tool according to claim 1 including a longitudinally extending insert mounted in the lumen of the shaft, the insert comprising a tubular body having a plurality of longitudinal sub-lumens formed therein, wherein each of the plurality of longitudinal sub-lumens breaks the outer surface of the tubular body.

18. The electrosurgical resector tool according to claim 17, wherein the coaxial transmission line comprises a coaxial cable mounted in a first sub-lumen of the tubular body.

19. The electrosurgical resector tool according to claim 17, wherein the actuator comprises a control rod slidably mounted in a second sub-lumen of the tubular body.

20. The electrosurgical resector tool according to claim 19, wherein the second sub-lumen has a low friction tube mounted therein, and wherein the control rod is slidably mounted in the low friction tube.

21. The electrosurgical resector tool according claim 1, wherein the instrument tip is dimensioned to fit within an instrument channel of a surgical scoping device.

22. The electrosurgical resector tool according to claim 1, wherein the upstanding tooth and/or the downwardly extending tooth are rounded in shape.

23. An electrosurgical apparatus comprising:

an electrosurgical generator for supplying radiofrequency (RF) electromagnetic (EM) energy and microwave EM energy;

a surgical scoping device having an instrument cord for insertion into a patient's body, the instrument cord having an instrument channel extending therethrough; and the electrosurgical resector tool according to claim 1 inserted through the instrument channel of the surgical scoping device.

24. The electrosurgical apparatus according to claim 23 having a handpiece for controlling the electrosurgical resector tool mounted at a proximal end of the shaft, wherein the handpiece comprises:

a body;

an actuating element slidably mounted on the body; and a rotator rotatably mounted on the body, wherein the coaxial transmission line and the shaft of the electrosurgical resection tool are mounted to slide relative to the body with the actuating element and rotate relative to the body with the rotator, wherein the actuator of the electrosurgical resection tool comprises a control rod extending through the lumen of the shaft, the control rod having a proximal portion that is mounted in a longitudinally fixed position relative to the body, wherein the actuating element is operable to control movement of the movable portion relative to the static portion, and wherein the rotator is operable to control rotation of the electrosurgical resector tool relative to the instrument channel.

25. The electrosurgical apparatus according to claim 24, wherein the handpiece includes a power input port on the actuating element, the power input port being connected to transfer power received therein to the coaxial transmission line.

26. The electrosurgical apparatus according to claim 25, wherein a connection direction into the power input port extends perpendicularly to the direction in which the actuating element is slidable relative to the body.

* * * * *